United States Patent
Fairclough et al.

(10) Patent No.: US 6,652,843 B2
(45) Date of Patent: Nov. 25, 2003

(54) ANTIPERSPIRANT COMPOSITIONS

(75) Inventors: Colette Marie Fairclough, Wirral (GB); Kevin Ronald Frankin, Wirral (GB)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 0 days.

(21) Appl. No.: 10/346,676

(22) Filed: Jan. 17, 2003

(65) Prior Publication Data

US 2003/0180240 A1 Sep. 25, 2003

(51) Int. Cl.$^7$ .............................. A61K 7/32; A61K 7/00
(52) U.S. Cl. .................... 424/65; 424/400; 424/401
(58) Field of Search .................... 424/65, 400, 401

(56) References Cited

U.S. PATENT DOCUMENTS

| | | | |
|---|---|---|---|
| 4,725,432 A | * 2/1988 | May ............................. | 424/66 |
| 5,169,626 A | * 12/1992 | Tanner et al. .................. | 424/66 |
| 5,232,689 A | 8/1993 | Katsoulis et al. .............. | 424/66 |
| 5,384,117 A | * 1/1995 | Vu et al. ....................... | 424/66 |
| 5,455,026 A | * 10/1995 | Bahr et al. .................... | 424/65 |

FOREIGN PATENT DOCUMENTS

| | | |
|---|---|---|
| EP | 665 007 | 8/1995 |
| WO | 93/23008 | 11/1993 |
| WO | 00/61079 | 10/2000 |
| WO | 01/58411 | 8/2001 |
| WO | 02/11692 | 2/2002 |

OTHER PUBLICATIONS

Great Britain Search Report in a GB application GB 0201163.3.
Great Britain Search Report in a GB application GB 0217840.8.
Great Britain Search Report in a GB application GB 0201164.1.
Caplus Abstract Accession No. 1998: 599614 & JP 100245315 A2 (Pola Chemical Industries) Sep. 14, 1998.
Caplus Abstract Accession No. 2001:668189 & JP 2001247451 A2 (Pola Chemical Industries Inc. & Nisshin Oil Mills Ltd.) Sep. 11, 2001.
Caplas Abstract Accession No. 1998:555702 & JP 10226615 A2 (Pola Chemical Industries Inc.) Aug. 25, 1998.

* cited by examiner

Primary Examiner—Shelley A. Dodson
(74) Attorney, Agent, or Firm—Kevin J. Stein

(57) ABSTRACT

Clear solid suspension antiperspirant compositions comprise 0.5 to 50% by weight of a particulate antiperspirant active material of which less than 50% by weight of its particles are below 110pm diameter and a refractive index of from 1.49 to 1.57 at 22° C. is suspended in a water-immiscible carrier liquid of which at least 50% by weight is selected from liquid non-volatile silicone oils and liquid alkyl-aryl esters and not more than 25% by weight of the carrier liquid comprises a volatile silicone oil. The carrier liquid and the antiperspirant have refractive indexes which differ by no more than 0.02 at 22° C and the structurant which solidifies the carrier liquid comprises a fibre-forming non-polymeric structurant, and preferably an N-acyl aminoacid amide such as GPl and/or a cyclodipeptide such as a thymol derivative of (2S-cis)-(–)-5-benzyl-3,6-dioxo-2-piperazine acetic acid.

32 Claims, No Drawings

ANTIPERSPIRANT COMPOSITIONS

FIELD OF THE INVENTION

The present invention relates to antiperspirant compositions for application to human skin, and to the preparation and use of such compositions.

BACKGROUND OF THE INVENTION AND SUMMARY OF PRIOR ART

A wide variety of cosmetic compositions for application to human skin make use of a structured liquid carrier to deliver an active material to the surface of the skin, including in particular antiperspirant or deodorant compositions which are widely used in order to enable their users to avoid or minimise wet patches on their skin, especially in axillary regions or to control or prevent the emission of malodours, which could otherwise arise when the user perspires.

Antiperspirant or deodorant formulations have been provided with a range of different product forms. One of these is a so-called "stick" which is usually a bar of an apparently firm solid material held within a dispensing container and which retains its structural integrity and shape whilst being applied. When a portion of the stick is drawn across the skin surface, a film of the stick composition is transferred to the skin surface. Although the stick has the appearance of a solid article capable of retaining its own shape for a period of time, the material often has a structured liquid phase so that a film of the composition is readily transferred from the stick to another surface upon contact.

Although structuring is a term that has often been employed in respect of materials which structure a carrier liquid, various other terms have been employed alternatively, including solidifying and gelling.

Antiperspirant sticks can be divided into three categories. Suspension sticks contain a particulate antiperspirant active material suspended in a structured carrier liquid phase which often is anhydrous and/or in many instances may be water-immiscible. Emulsion sticks normally have a hydrophilic phase, commonly containing the antiperspirant active in solution, this phase forming an emulsion with a second, more hydrophobic, liquid phase. The continuous phase of the emulsion is structured. Solution sticks typically have the antiperspirant active dissolved in a structured liquid phase which is polar and may comprise a polar organic solvent, which is often water-miscible, and the polar phase can contain water.

There is substantial literature on structuring of antiperspirant or deodorant compositions.

Conventionally, many suspension sticks have been structured using naturally-occurring or synthetic waxy materials, in which term we include materials which resemble beeswax, in that they soften progressively with increase in temperature until they are fluid, generally by about 95° C. Examples of wax-structured sticks are described in an article in Cosmetics and Toiletries, 1990, Vol 105, P75–78, in U.S. Pat. Nos. 5,169,626 and 4,725,432 and in many other publications, in some of which such materials are called solidifying agents.

More specifically, it has been common practice for suspension sticks to be structured or solidified by incorporating fatty alcohol into the composition, often accompanied by a smaller amount of castor wax. Sticks which are structured with fatty alcohol tend to leave visible white deposits on application to human skin; moreover the deposits can also transfer onto clothing when it comes into contact with the skin and the wearer can, for example, find white marks at the armhole of the sleeveless garment. Fatty alcohols are often regarded as coming within the general category of waxy materials, but we have observed that they are a more significant source of white deposits than various other waxy materials. Consumer tests have identified that such white marks are disliked by some consumers and indeed, at least in some countries a market has developed for antiperspirant products which leave little or no such apparent marks on application to the skin.

Patent literature has also proposed the preparation of a suspension composition that not only does not leave visible marks upon skin application, but additionally is clear. Thus, for example Vu et al in U.S. Pat. No. 5,384,117 disclose anhydrous antiperspirant compositions in which a particulate antiperspirant is suspended in a liquid carrier having a matched refractive index to within about 0.02 such that the resultant composition has a relative turbidity of less than 800 FTU. The text exemplified the use of a polyethylene-vinyl acetate copolymer (AC-400 from Allied Corp) as gelling agent to solidify compositions containing various aluminium chlorohydrates antiperspirants, but did not exemplify any other structurants. Even a polyethylene homopolymer that was mentioned as an alternative was not exemplified, though the inventor was under a duty to disclose the best mode of operating the invention. It will be recognised that the text provides no teaching to the skilled man as to how to identify an alternative to the polyethylene-vinyl acetate copolymer.

It would be desirable to find an alternative structurant to the polymers exemplified by Vu for several reasons. First, the polymer exemplified by Vu is not a particularly effective structurant for water-immiscible liquids. The instant inventors found that gels produced using 20 parts by weight of AC-400A to 80 parts by weight of water-immiscible liquid containing a significant fraction of silicone oils were rather soft rather than firm at ambient temperature, even though that is a high weight ratio of structurant to carrier liquid. Moreover the gels produced appeared to be opaque when the refractive indexes of the carrier liquids were similar to those in Vu's Examples. Vu also discloses potential processing difficulties with polymer gellants, including the need to prevent the carrier fluid/gellant mixture exceeding its cloud point.

The difficulty of creating a clear suspension stick which employs a non-polymeric material can be seen from the fact that many readily available non-polymeric gellants render a water-immiscible liquid carrier opaque when it is solidified by them. Such agents include many of the waxes and similar materials to which reference has been made hereinabove.

The difficulty of obtaining clear solidified compositions is further compounded by the fact that antiperspirant actives tend to have a refractive index that is significantly higher than conventional silicone oils, including particularly volatile silicone oils, such as cyclomethicones that have a refractive index just below 1.4, or even those commercially available non-volatile polyphenylmethylsiloxane liquids such as Dow Corning DC-556 which have an intermediate refractive index of around 1.45. Such a low refractive index renders it difficult to obtain sufficiently close refractive index matching to permit the resultant suspension to be clear without some additional carrier being employed. This becomes a greater problem as the refractive index of the antiperspirant increases, for example when employing an activated aluminium chlorohydrate instead of an aluminium chlorohydrate. Moreover, the overall difficulty of selecting a liquid carrier is exacerbated at least in part because antiperspirant compositions are left in place on the skin for long periods between washing, often all day, so that the other properties of a prospective liquid carrier must be kept in mind as well.

The problem of refractive index matching of active and carrier is at its worst for aluminium-zirconium antiperspirants which have the highest refractive index of conventional aluminium-containing antiperspirant actives, if the producer wishes to avoid alkoxycinnamate compounds such as octylmethoxy cinnamate, that have known disadvantage characteristics for leave on skin product (such as an antiperspirant) of colour, irritancy and possible toxicity. The skilled man would be prejudiced against employing the compositions of Vu's Examples 1 to 12 on account of the presence of at least 13.5% up to 72.3% by weight of an alkoxy cinnamate therein. The skilled man can also recognise that Vu's polymer would cause a suspension of aluminium-zirconium antiperspirant in to be opaque, even if he matched exactly the refractive indexes of carrier and antiperspirant, in view of the low refractive index of the polymer. That explains the absence from Vu of any Examples employing simultaneously polymer and aluminium-zirconium antiperspirant.

In U.S. Pat. Nos. 5,455,026 and 5,492,691, Bahr et al disclosed the formation of clear antiperspirant gels. Bahr set out various criteria, including selection of the same refractive index (RI) range for the antiperspirant active and the blend of carrier fluids, the matching of those RIs and it was also essential to select 12-hydroxystearic acid (12-HSA) or a salt thereof as gelator. Translucent gels were obtained, in their Examples 2 and 3 by matching absolutely the RI of the disperse particulate antiperspirant and the carrier fluid. However, where there was even a small difference in RI between the particles and the carrier fluid, 0.014 as in Comparative Example 4, the resultant composition was no longer clear, demonstrating much higher turbidity (the maximum on the scale 1000, compared with 240 and 272 respectively.

Three problems remain compared with Bahr's disclosure. How can clarity be improved even when the RI matching is not absolute? How can clarity be achieved in anhydrous stick formulations employing water-immiscible oils as carrier for a particulate antiperspirant which are solidified by structurants other than 12-HSA? This problem relates to both clarity of the composition and formation of a stick. It will be recognised that, as mentioned previously herein, the materials disclosed in U.S. Pat. No. 5,348,117 were found to form soft rather than firm antiperspirant compositions. Thirdly, how can clear formulations be obtained which are not restricted to the range of RIs described by Bahr?

The instant inventors have recognised that any alternative structurant that is employed with the intention of obtaining a clear solid suspended antiperspirant product would ideally not only be capable of being refractive-index matched with the remaining constituents of the composition, but also that it should be a relatively tolerant to a change in the matched refractive index of carrier and antiperspirant, because it is considerably more difficult to match the refractive indexes of three components very closely, compared with only two. This enables a wider window of refractive index matched antiperspirant/carrier liquid to be employed and to cater for variations in RI which can arise in formulations, for example due to temperature changes or small variations between batches of ingredients, a matter of practical significance in full-scale manufacture.

Bahr discloses the suspension of a particulate antiperspirant salt having an RI of 1.510 or 1.514 and an undefined particle size distribution suspended in a carrier oil blend having an RI completely matched to the RI of the antiperspirant salt and gelled using solely 12-HSA. Such a combination is manifestly not within the present invention.

Objects of the present invention

It is an object of the present invention to ameliorate or overcome one or more of the problems identified hereinabove, for example on or more of the problems relative to the disclosure in U.S. Pat. Nos. 5,455,026/5,492,691 or to the disclosure in U.S. Pat. No. 5,348,117.

It is an object of the present invention to provide structured solid antiperspirant compositions, which demonstrate clarity, but which do not employ polymer structurants. A further object of some embodiments of the invention is to provide solid suspension aluminium-zirconium antiperspirant compositions of improved clarity.

When the instant inventors employed a particular class of structurants which they had found to be capable of providing the above-mentioned desirable wider RI window, they found that the particle size of the antiperspirant salt has a substantial and significant impact upon the clarity of the resultant suspension. Intuitively, it would be expected that smaller particles ought to be beneficial, but the situation in the real world is more complicated than that, and indeed, to at least some extent, is contrary to intuition. It will be recognised that Bahr in his US patents was silent concerning the particle size distribution of antiperspirant salts and manifestly was not aware of its potential significance.

Various structurants for water-immiscible oils as carrier fluids for suspended particulate antiperspirant salts have been disclosed in U.S. Pat. Nos. 6,231,841, 6,248,312, 6,251,377, 6,410,001, 6,410,003, and 6,458,344. None of said specifications disclose the instant invention.

SUMMARY OF THE INVENTION

Applicants have now found that clear solid suspension antiperspirant compositions can be obtained by employing together a selected class of carrier liquids, a selected class of structurants and particulate antiperspirant materials which satisfy a specified criterion.

Broadly, in a first aspect of the present invention, there is provided a clear anhydrous solid antiperspirant composition comprising from 0.5 to 50% by weight of a particulate antiperspirant salt suspended in a water-immiscible liquid carrier that is solidified by an effective amount of a structurant characterised in that:- i) the particulate antiperspirant contains less than 50% by weight of particles having a diameter of up to 10 $\mu$m and a refractive index of from 1.49 to 1.57 at 22° C., ii) at least 50% by weight of the carrier liquid is selected from liquid non-volatile silicone oils and liquid alkyl-aryl esters ii) not more than 25% by weight of the carrier liquid comprises a volatile silicone oil, iv) the carrier liquid and the antiperspirant have refractive indexes which differ by no more than 0.02 at 22 C. and v) the structurant comprises a fibre-forming non-polymeric structurant.

Herein, the term "clear" in respect of antiperspirant compositions indicates that at least 0.5% of light having a wavelength of 580nm at 22° C is transmitted through a 1cm sample.

A composition of this invention will generally be marketed in a container by means of which it can be applied at time of use. This container may be of conventional type.

By production of the composition in accordance with the criteria of the present invention, it is possible to obtain anhydrous antiperspirant suspension sticks which exhibit improved clarity compared with corresponding compositions in which, for example, the antiperspirant salt has a similar mean particle size but a different particle size distribution, and in particular when RI matching is not complete.

A second aspect of the invention therefore provides an antiperspirant product comprising a dispensing container having an aperture for delivery of the contents of the container, means for urging the contents of the container through the said aperture, and a composition of the first aspect of the invention in the container.

Means for urging the contents of the container to the said aperture or apertures, for flow through them, may be moving parts operable by the user or an orifice in the container opposite said aperture providing digital access. If desired, the container may itself be made from a clear material, possibly tinted, so that a consumer may recognise in pack that the composition is clear.

The compositions of this invention can be produced by conventional processes for making antiperspirant suspension solids.

Thus, according to a third aspect of the present invention there is provided a process for the production of a cosmetic composition comprising the steps of:

a1) incorporating into a water-immiscible liquid carrier a structurant which is one or more structurant compounds as defined in the composition of the first aspect, a2) mixing the liquid carrier with a particulate antiperspirant active as described in the first aspect, a3) heating the liquid carrier or a mixture containing it to an elevated temperature at which the structurant is dissolved or dispersed in the water-immiscible liquid carrier, steps a1) a2) and a3) being conducted in any order followed by:

b1) introducing the mixture into a mould which preferably is a dispensing container, and then c1) cooling or permitting the mixture to cool to a temperature at which-the liquid carrier is solidified.

According to the fourth aspect, there is provided a cosmetic method for preventing or reducing perspiration or odour formation on human skin comprising topically applying to the skin a composition comprising an antiperspirant active, a water-immiscible liquid carrier and, a structurant compound as described above in the first aspect.

DETAILED DESCRIPTION AND EMBODIMENTS

As mentioned hereinabove, in accordance with the first aspect, the invention requires a structurant compound to solidify a water-immiscible liquid phase and a particulate antiperspirant suspended therein. Other materials may also be present depending on the nature of the composition. The various materials will now be discussed by turn and preferred features and possibilities will be indicated.

The structurant compounds of the present invention are fibre-forming non-polymeric materials. It is characteristic of such structurants that:

they are able to gel the organic liquid in the absence of any disperse phase, when used in sufficient quantity not exceeding 15% by weight;

the structured liquids are obtainable by cooling from an elevated temperature at which the structurant is in solution in the liquid—this hot solution being mobile and pourable;

the (thus obtained) structured liquid becomes more mobile if subjected to shear or stress;

the structure does not spontaneously recover within 24 hours if the sheared liquid is left to stand at ambient laboratory temperature, even though a small partial recovery may be observed;

the structure can be recovered by reheating to a temperature at which the structurant is in solution in the liquid and allowing it to cool back to ambient laboratory temperature.

It appears that such structurants operate by interactions which are permanent unless disrupted by shear or heating. Such structurants form a network of fibres (sometimes called strands) extending throughout the gelled liquid. In some cases these fibres can be observed by electron microscopy, although in other cases the observation of the fibres which are believed to be present may be prevented by practical difficulties in preparing a suitable specimen. When observed, the primary fibres in a gel are generally thin (diameter less than 0.5 $\mu$m, often less than 0.2 $\mu$m) and can appear to have numerous branches or interconnections. Primary fibres may entwine to form a thicker strand.

Such non-polymeric structurants are generally monomers or dimers with molecular weight below 10,000, often below 5,000 and many of which below 1,000, rather than polymers which latter commonly have more than four repeat units and/or a molecular weight above 10,000.

The fibre-forming structurants employed herein preferably are selected from amide fibre-forming structurants and sterol fibre-forming structurants.

Within the term amide fibre-forming structurants are included such structurants that comprise amides of 12-hydroxy stearic acid, N-acyl aminoacid amides, amide derivatives of di and tribasic carboxylic acids, di-amide 1,2 or 1,3 substituted cyclohexane compounds, 1,3,5-triamido-substituted cyclohexane (both —CO—NH—R' and —NH—CO—R') and cyclodipeptides. Within the term sterols is included lanosterol.

Amides of 12-hydroxy stearic acid are described in U.S. Pat. No. 5,750,096, which description and the method of manufacture of such amides described therein is incorporated herein by reference. The alcohol used to form such an ester or the amine used to form such an amide may contain an aliphatic, cycloaliphatic or aromatic group with up to 22 carbons therein. If the group is aliphatic it preferably contains at least three carbon atoms. A cycloaliphatic group preferably contains at least five carbon atoms and may be a fixed ring system such as adamantyl. Other fatty acids with $C_8$ or longer alkyl chains may be used and amides thereof can also be used. A specific example is lauric monoethanolamide also termed MEA lauramide:

N-acyl aminoacid amides are described in U.S. Pat. No. 3,969,087. The list of such amides and their method of manufacture described in said patent specification in column 1 line 63 to column 4 line 47 and the amido derivatives named in Example of column 6 to 8, are incorporated herein by reference. N-Lauroyl-L-glutamic acid di-n-butylamide, employed in Example 14 of '087, is an especially desirable amide structurant for employment in the instant invention compositions and is commercially available from Ajinomoto under their designation GP-1.

A further class of amide structurants suitable for employment herein comprises amide derivatives of di and tribasic carboxylic acids, in accordance with the description set forth in WO 98/27954 notably alkyl N,N'dialkyl succinamides. Such description is incorporated herein by reference.

A yet further class of amide structurants comprises amido-containing compound of the general formula

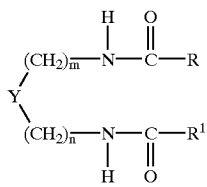

in which R and $R_1$ each independently denote a branched or unbranched moiety containing 5 to 27 carbon atoms, m and n are each independently, zero or 1, Y is a cyclohexane ring bearing the amido-containing substituent groups

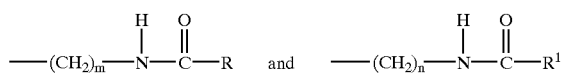

in 1,2 or 1,3 positions. Such amido-structurants and their method of preparation are described in EP-A-1177784 (due to be published in February 2002) on pages 11 to 13 and Example 1, which description is incorporated herein by reference.

A yet further class of amide structurants comprises 1,3, 5-triamido-substituted cyclohexane (both —CO—NH—R' and —NH—CO—R'). Such compounds and their preparation are described more fully in EP-A-1068854, in column 3, line 24 to column 4 line 47, which passage is incorporated herein by reference.

A still further class of amide structurants suitable for employment in the instant invention comprises structurants which satisfy the following general formula:-

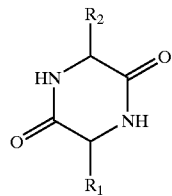

in which one of $R_1$ and $R_2$ represents an alkyl, alkyl ester group and the other represents an alkyl or alkaryl group. Examples of such amides are described in two papers by Hanabusa et al, entitled respectively Cyclo(dipeptide)s as low molecular-mass Gelling Agents to harden Organic Fluids, J. Chem Soc. Commun., 1994 pp1401/2, and Low Molecular Weight Gelators for Organic Fluids: Gelation using a Family of Cyclo(dipeptide)s, in the Journal of Colloid and Interface Science 224, 231–244 (2000), which descriptions of amide structurants are incorporated herein by reference.

However, it is especially preferred to employ herein a sub-class of cyclodipeptides not expressly disclosed by Hanabusa, which sub-class satisfies the general formula:-

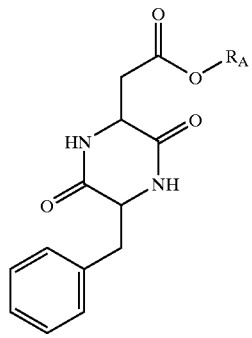

in which $R_A$ represents a carbocyclic or heterocyclic group containing not more than 2 rings. Such materials are sometimes herein referred to as DOPA derivatives. C) COM In DOPA derivatives, $R_A$ can comprise two fused rings, but preferably comprises a single six membered ring, either carbocyclic or heterocyclic, or a bridged ring. When A is carbocylic, it can be either saturated or unsaturated, preferably unsaturated or aromatic. When $R_A$ is heterocyclic, it is preferably saturated.

Although the cyclic group within $R_A$ can be unsubstituted, it is preferably substituted by at least one alkyl substituent, which preferably contains no more that 16 carbon atoms. In some highly desirable embodiments the alkyl substituent has a longest chain length of up to 4 carbon atoms, and in certain or those a total carbon content of up to 5 carbon atoms. The alkyl substituent may be linear or branched. Preferred examples include methyl, ethyl, propyl, isopropyl, butyl isobutyl or t-butyl or isopentyl. In a number of very suitable DOPA derivatives, $R_A$ contains two or more alkyl substituents and especially those selected from the above list of preferred examples. The alkyl substituents may be the same, such as two or more methyl substituents, or may be a combination of different substituents such as a methyl and isopropyl substituents. When $R_A$ is saturated, the substituents may depend from the same carbon atom in the ring, such as two methyl groups, or from different carbon atoms. In several highly desirable derivatives, two alkyl substituents are meta or para to each other, for example meta methyl groups or a para methyl and isopropyl group. In yet other derivatives, the ring may include a methylene bridge, which preferably likewise completes a six membered ring.

In some suitable DOPA derivatives, the or one alkyl substituent may be ortho or para to the bond with the DOPA residue, as in 4-methyl-phenyl-. In some or other DOPA derivatives, the bond with the DOPA residue is meta to one or preferably two methyl substituents.

When $R_A$ is heterocyclic, the heterocyclic atom is suitably nitrogen. Conveniently, the heterocyclic atom can be para to the bond with the DOPA residue. Moreover, in a number of desirable derivatives, the heteroatom is ortho to at least one alkyl group, better in a saturated ring and especially to up to 4 ortho methyl groups.

The group $R_A$ is often most easily referred to as the residue from the corresponding alcohol which may be reacted with DOPA to form the ester linkage. Thus, desirable examples of $R_A$ include the residues from 4-alkyl phenol, such as 4-nonyl-phenol, and 2,6-dialkyl- or 2,2,6,6-tetraalkyl-4-piperidinol, such as 2,2,6,6-tetramethyl-4-piperidinol.

In some preferred DOPA derivatives, the ring in $R_A$ is carbocyclic, and is substituted by at least two alkyl groups of which at least one is methyl and the other or one of the others is isopropyl. Examples of such preferred $R_A$ residues include menthol, isopinocamphenol and 3,5-dialkyl cyclohexanol such as 3,5-dimethyl cyclohexanol. Especially preferred $R_A$ residues include thymol. Yet others include the DOPA derivatives from carveol and carvacrol.

The DOPA derivatives used in this invention may be a mixture of compounds within the general formulae given, or may be a single compound.

The DOPA derivatives can be prepared by reacting the respective alcohol with DOPA in acid form (DOPAA), or possibly with an acid chloride, or possibly an anhydride or an ester containing a DOPA residue. DOPAA can be obtained by cyclising aspartame. DOPAA can be reacted with the relevant alcohol of formula $R_A OH$, preferably in a mole ratio to the DOPAA of at least 2:1 in dimethyl sulphoxide, in a ratio of from 6:1 to 12:1, in the presence of a promoter, such as a carbonyldiimidazole, in an amount preferably from 0.5 to 2 moles of promoter per mole of DOPA acid. The reaction is conveniently carried out at a temperature from 40 to 60° C.

Herein, it is more desirable to employ N-acyl amino acid amides and/or cylodipeptides, and especially desirable to employ N-acyl amino acid amides and/or cylodipeptides which are DOPA derivatives. In a number of desirable embodiments the cyclic dipeptide and N-acyl aminoacid amide are present at a weight ratio in the range of from 1:1 to 1:12.

Lanosterol, as disclosed in U.S. Pat. No. 6,251,377 may suitably be used if the water-immiscible liquid is predominantly silicone oil. Lanosterol has the following chemical formula:-

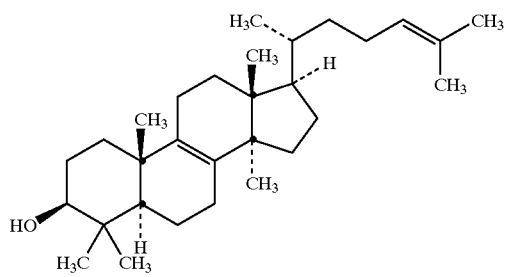

It is commercially available, e.g. from Croda Chemicals Ltd, and as supplied it contains some dihydrolanosterol. This impurity in the commercial material does not need to be removed.

The amount of the said fibre-forming structurant in a composition of this invention is likely to be from 0.5 to 15% by weight of the whole composition and preferably from 1% up to 10%. Herein, unless other wise stated, a % is by weight based on the entire composition. Advantageously, by a suitable choice of structurants or mixture of structurants, it is possible to obtain stick compositions of acceptable firmness without the structurant exceeding 10% by weight of the composition or 15% by weight of the carrier liquid plus structurant. This represents a particular benefit for the composition, compared for example with the use of the polymer structurants of U.S. Pat. No. 5,348,117 discussed hereinbefore. This is beneficial, not only because it reduces the cost of the structurant, often a relatively expensive ingredient, but also releases formulation space for incorporating other desirable ingredients in the composition and furthermore reduces the amount of ingredient which might contribute to lack of clarity or visible deposits.

It is especially desirable herein to employ the DOPA derivatives in an amount of at least 0.3% and in many instances not more than 2%. In some especially desirable embodiments, the amount of DOPA derivatives is from 0.5% to 1.6%. Such amounts or ranges of the DOPA derivative are suitable for the material by itself, or when employed in combination with some other fibre-forming structurant such as the N-acyl aminoacid.

In some or other embodiments of the present invention it can be advantageous to employ N-acyl aminoacids and especially N-lauroyl-L-glutamic acid di-n-butylamide in an amount of from 1% to 7.5%, and especially at least 2.0% or 2.5%. In many instances not more than 6% of the N-acyl aminoacid amide is needed to achieve a satisfactory stick hardness. Such amounts or ranges of the N-acyl amino acid are suitable for the material by itself, or when employed in combination with some other fibre-forming structurant such as a DOPA derivative. The proportion of structurant such as amido structurant to employ can alternatively be expressed in relation to the proportion of water-immiscible liquid carrier or carrier mixture which is employed. On that basis, the proportion of such a structurant is desirably from 2 to 12%, and in many instances is selected in the range of from 4 to 8% by weight of the water-immiscible carrier.

A dibenzylidene alditol such as dibenzylidene sorbitol can be employed together with an amide structurant. The dibenzylidene alditol is conveniently employed at a concentration selected in the range of from 0.1 to 0.5% by weight. The weight ratio of the dibenzylidene alditol to amide structurant is often in the range of from 1:3 to 1:10.

An advantage of the selected structurants, such as the amido structurants, e.g. cyclodipeptides of N-acylaminoacid amides, or lanosterol, is that the light transmission through compositions that are structured with them tend to be relatively insensitive to changes in the RI of the carrier liquids. By insensitive is meant that the transmission does not fall away steeply from a peak, but instead only relatively slowly. Thus, not only do the structurants according to the present invention exhibit peak light transmission at a refractive index that is similar to or within the range of refractive indexes of the antiperspirant active, but also its insensitivity to RI change in the carrier liquid (mixture) means that the problem of RI matching in the composition is simplified.

Carrier liquid

The water-immiscible carrier liquid comprises one or a mixture of materials which are relatively hydrophobic so as to be immiscible in water. Some hydrophilic liquid may be included in the carrier, provided the overall carrier liquid mixture is immiscible with water, but it is commonly absent or at most 3% of the mixture. It will generally be desired that this carrier is liquid (in the absence of structurant) at temperatures of 15EC and above, up to at least the temperature at which the structurant dissolves, such as up to 130° C. It may have some volatility but its vapour pressure will generally be less than 4 kPa (30 mmhg) at 25° C. so that the material can be referred to as an oil or mixture of oils. More specifically, it is desirable that at least 80% and in many instances from 90% to 100% by weight of the hydrophobic carrier liquid should consist of materials with a vapour pressure not over this value of 4kPa at 25° C.

In many compositions herein, it is highly desirable to employ a mixture of carrier liquids, since by adjusting the weight ratio of the individual carrier liquids to each other, it is possible easily to achieve a desired refractive index for the mixture which is proportionately intermediate between the refractive indexes of the respective carrier liquids, and appropriately matched with the antiperspirant active which is intended to be suspended therein.

In particular, the carrier liquid or mixture of liquids satisfies the following criteria:-

At least 50% by weight of the carrier liquid is selected from liquid non-volatile silicone oils and liquid alkyl-aryl esters and not more than 25% by weight of the carrier liquid comprises a volatile silicone oil, i.e. liquid polyorganosiloxane. To class as "volatile" such material should have a measurable vapour pressure at 20 or 25EC. Typically the vapour pressure of a volatile silicone lies in a range from 1 or 10 Pa to 2 kPa at 25° C.

Although it is desirable to include a volatile silicone because it gives a "drier" feel to the applied film after the composition is applied to skin, such materials have an inherently low refractive index which renders it more difficult to achieve acceptably close refractive index matching between the carrier fluid and the suspended antiperspirant salt as the proportion of the volatile silicone increases.

Volatile polyorganosiloxanes can be linear or cyclic or mixtures thereof. Preferred cyclic siloxanes include polydimethylsiloxanes and particularly those containing from 3 to 9 silicon atoms and preferably not more than 7 silicon atoms and most preferably from 4 to 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $10^{-5}$ m$^2$/sec (10 centistokes), and particularly above $10^{-7}$ m$^2$/sec (0.1 centistokes), the linear siloxanes normally exhibiting a viscosity of below $5 \times 10^{-6}$ m$^2$/sec (5 centistokes). The volatile silicones can also comprise branched linear or cyclic siloxanes such as the aforementioned linear or cyclic siloxanes substituted by one or more pendant —O—Si(CH$_3$)$_3$ groups. Examples of commercially available silicone oils include oils having grade designations 344, 345, 244, 245 and 246 from Dow Corning Corporation; Silicone 7207 and Silicone 7158 from Union Carbide Corporation; and SF1202 from General Electric.

The proportion of volatile silicone oils in the composition is often less than 5%, and in many instances not more than 3% or from 0 to 1% by weight of the composition.

The non-volatile silicone oils, which are employed in compositions herein can include polyalkylsiloxanes, polyalkylaryl siloxanes and polyethersiloxane copolymers. These can suitably be selected from dimethicone oils and dimethicone copolyol oils. Commercially available non-volatile silicone oils include products available under the trademarks Dow Corning 556 and Dow Corning 200 series.

It will be recognised that in the selection of oils to act as carrier fluid, the refractive index of the oil is of great importance, because the oil or its mixture with some other carrier fluid will be refractive index matched with the antiperspirant active as described more fully elsewhere herein. Consequently, it is especially desirable to employ non volatile aryl-substituted silicone oils that have a refractive index of at least 1.5, abbreviated herein to RIAS silicone oils in respect of at least a fraction of the non-volatile silicone oils. Such RIAS silicone oils are often linear, and commonly contain a significant fraction of aryl groups, such as phenyl, though not exclusively phenyl, in addition to alkyl groups, such as methyl. The proportion and choice of aryl substituents enables the refractive index of at least 1.5 to be achieved. A suitable example of a RIAS silicone oil is a linear phenyl/methyl substituted polysiloxane designated by the supplier Dow Corning Inc under its trademark DC704. Such RIAS silicone oils of high refractive index preferably constitute at.least 50% by weight of the non-volatile silicone oils, up to 100% and particularly from 60 to 100%. This renders it easier to achieve refractive index matching with antiperspirant actives having a comparatively high refractive index in a carrier mixture that is readily structured by the structurant(s) according to the present invention. The balance of the non-volatile silicone oils can comprise other non-volatile silicone oils of lower refractive index.

The non-volatile silicone oils, and especially the above-mentioned RIAS silicone oils, can constitute up to 100% by weight of the carrier liquids, preferably at least 40% by weight, better at least 50% by weight and particularly from 65 or 70 to 85% by weight. The residue can comprise at least partly the alkyl-aryl esters which will be described more fully hereinafter and optionally volatile silicone oils. However, the residue preferably includes at least some liquid aliphatic water-immiscible alcohol, described more fully hereinbelow. Incorporation of such a water-immiscible alcohol in the carrier mixture is particularly suitable when an amide structurant is employed. When lanosterol is employed, then it is most desirable to employ solely silicone oils or not less than 97% silicone oils.

The liquid carrier in the invention compositions can comprise the liquid alkyl-aryl esters having a melting point of below 20EC, include fatty alkyl benzoates. Examples of such esters include suitable C8 to $C_{18}$ alkyl benzoates or mixtures thereof, including in particular $C_{12}$ to $C_{15}$ alkyl benzoates eg those available under the trademark Finsolv. Incorporation of such alkyl benzoate esters as at least a fraction of the hydrophobic carrier liquid can be advantageous, because they can raise the average refractive index of the mixture compared with using volatile—silicone—containing carriers, and thereby render it easier to obtain translucent or transparent formulations.

It can also be desirable for the carrier mixture to include a fraction of liquid aliphatic water-immiscible alcohols. Such aliphatic alcohols are branched having a chain length of at least 10 carbons, and a melting point that is not above 20° C. Many suitable ones contain from 14 to 30 carbons. Suitable examples include isostearyl alcohol and octyldodecanol. Such alcohols can suitably comprise up to 35% by weight of the carrier liquids, for example at least 5%, often at least 10% and in many instances from 15 to 30%. As mentioned previously, such alcohols are of particular benefit when the structurant comprises an amido compound, including cyclodipeptide derivatives, N-acylaminoacid amides and amido-substituted cyclohexane compounds.

It is particularly desirable to employ liquid carrier systems in conjunction with an amide structurant which consist of at least 60% RIAS silicone oils such as 70 to 85%, from 15 to 30% branched water-immiscible aliphatic alcohols and the balance, if any, being either other silicone oils or fatty alkyl benzoates. Such carrier mixtures are particularly suited to enable refractive index matching with a number of antiperspirant actives, such as activated aluminium chlorohydrates.

It is highly desirable if the invention compositions are free from, or at worst contain not more than a small proportion such as 3% by weight (of the carrier mixture) of alkoxy cinnamates, including specifically octylmethoxy cinnamate or isoamylmethoxy cinnamate. This avoids completely or at least minimises any impairment to the compositions by virtue of the irritant or toxic properties of such compounds.

Antiperspirant Actives

The composition preferably contains an antiperspirant active. Antiperspirant actives, are preferably incorporated in an amount of from 0.5–50%, particularly from 5 to 30% or 40% and especially from 5 or 10% to 30% of the weight of the composition. It is often considered that the main benefit from incorporating of up to 5% of an antiperspirant active in a stick composition is manifest in reducing body odour, and that as the proportion of antiperspirant active increases, so the efficacy of that composition at controlling perspiration increases.

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates.

Aluminium halohydrates are usually defined by the general formula $Al_2(OH)_xQ_y \cdot wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever NV et al), the contents of which specification is incorporated herein by reference. Such activated aluminium chlorohydrates are made by a method in which the weight concentration of aluminium compounds in the solution is controlled within specified limits and simultaneously the temperature of that solution is controlled within a specified elevated temperature range whilst polymeric aluminium species are formed, and drying conditions are strictly controlled as described in the said EP-A-6739. Some activated salts do not retain their enhanced activity in the presence of water but are useful in substantially anhydrous formulations, i.e. formulations that do not contain a distinct aqueous phase.

Zirconium actives can usually be represented by the empirical general formula: $ZrO\ (OH)_{2n-nz}B_z \cdot wH_2O$ in which z is a variable in the range of from 0.9 to 2.0 so that the value 2n−nz is zero or positive, n is the valency of B, and B is selected from the group consisting of chloride, other halide, sulphamate, sulphate and mixtures thereof. Possible hydration to a variable extent is represented by $wH_2O$. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have co-ordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_2(NH_2)COOH$.

It is highly desirable to employ complexes of a combination of aluminium halohydrates and zirconium chlorohydrates together with amino acids such as glycine, which are disclosed in U.S. Pat. No. 3,792,068 (Luedders et al). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from Westwood, from Summit and from Reheis, though with differing particle size distributions. Consequently, such actives would become suitable for employment in the instant invention if their production has been suitably adapted to meet the invention particle size criteria.

The proportion of solid antiperspirant salt in a suspension composition normally includes the weight of any water of hydration and any complexing agent that may also be present in the solid active.

The particulate antiperspirant employed in the instant invention has a refractive index (RI) of at least 1.49 and not higher than 1.57. Actives which are free from zirconium tend to have an RI of from 1.49 to 1.54, depending on their formula and at least partly on their residual water content. Likewise, actives which contain zirconium tend to have an RI of from 1.52 to 1.57. The water content of the antiperspirant active can be modified by hydration after dried active has been made or by drying to an intermediate water content. The actives can also be treated with a small amount of an alcohol such a C2 to C4 aliphatic alcohol, eg ethanol, to alter its RI.

Herein, the RIs of the antiperspirant active and the suspended antiperspirant active are matched to within 0.02. Herein, RIs and differences between them are those at 22° C. unless otherwise specified. Preferably, the difference between the refractive indices is less than 0.01 and especially less than 0.005. This can be achieved by varying the proportions of liquids constituting the carrier, its resultant RI being a weight averaged RIs of the carrier constituents and/or by varying the RI of the antiperspirant active as indicated above. Under many circumstances, RI matching of the constituents of the invention formulations is not absolutely perfect. Small variations can arise in practice, for example from changes in temperature or between different batches of ingredients. Thus, such RI difference in the invention compositions herein on the shelf or in the home is often at least 0.0005, and sometimes at least 0.001. Advantageously, by selecting the particulate antiperspirant active in accordance with the criteria described herein, and particularly with increasingly preferred criteria, the benefit of clear formulations can be retained even when the above-mentioned RIs do not match exactly.

The antiperspirant active employed herein comprises small particles, of which not more than 50% by weight have a diameter of below 10 μm. Preferably less than 40% and more preferably less than 25% of particles by weight have a particle size of below 10 μm. In practice, desirable antiperspirant actives contain at least 1% and often at least 5% by weight of particles in the range of from 1 to below 10 μM. In general, at least 90% by weight of the antiperspirant active has a particle size of below 100 μm, in many instances at least 95% by weight and in some preferred compositions at least 99% by weight below 100 μM. In many embodiments herein, the active has a weight average particle size of from 12 to 50 μm. It will be recognised, though that materials having such an average particle size are suitable only if they also meet the criterion given above about maximum proportion of particles below 10 μm.

The fineness, coarseness and particle size distribution of antiperspirant actives that are produced can vary substantially, depending on their manner and conditions of manufacture, including the type of drying stage employed, and any subsequent processing stages, such as milling, and/or classification. Actives having an appropriate particle size distribution to satisfy the above selection criterion can be made by suitably controlling conventional drying and milling techniques in manners known to persons skilled in the art of making antiperspirant actives, so as to reduce the proportion of particles produced of sub 10 μm diameter. Methods can include control of droplet size in spray drying. Where a product is produced, for example by spray drying or freeze drying that has excessive proportion of sub 10 μm diameter particles, the proportion can be lowered by conventional classification apparatus.

Furthermore, it is highly desirable to employ antiperspirant active material which is free or substantially free from hollow particles. In this context, substantially free indicates a content of less than 10% by weight hollow spheres, and preferably less than 5% by weight. Some drying techniques, eg spray drying, can produce materials which contain greater than such a proportion of hollow spheres. The proportion of hollow spheres in an antiperspirant material can be reduced by milling the particulate material, such as by ball or swing milling.

Optional ingredients

Optional ingredients include wash-off agents, often present in an amount of up to 10% w/w to assist in the removal of the formulation from skin or clothing. Such wash-off agents are typically nonionic surfactants such as esters or ethers containing a $C_8$ to $C_{22}$ alkyl moiety and a hydrophilic moiety which can comprise a polyoxyalkylene group (POE or POP) and/or a polyol.

The compositions herein can incorporate one or more non-particulate cosmetic adjuncts conventionally contemplatable for cosmetic solids. Such cosmetic adjuncts can include deodorant actives, such as in an amount of up to 2%, skin benefit agents such as allantoin or lipids, for example in an amount of up to 5%; colours; skin cooling agents, such menthol and menthol derivatives, often in an amount of up to 2%, all of these percentages being by weight of the composition. A commonly employed adjunct is a perfume, which is normally present at a concentration of from 0 to 4% and in many formulations from 0.25 to 2% by weight of the composition.

A further class of optional ingredients can comprise particulate suspending aids or fillers, though normally in an amount of not more than 5% by weight. Such aids or fillers, which can include silicates, clays or talc, most desirably are selected to have a refractive index which is similarly matched to that of the antiperspirant active and the carrier fluid mixture, so that the maximum RI difference between particulate or carrier constituents of the composition is within the range or preferred range of RI difference between the RIs mentioned hereinbefore.

Product Form

The sticks produced herein are clear, the extent of light transmission depending at least partly on the extent to which the refractive indices (RI) of the ingredients are matched and the particle size of the particulate antiperspirant is controlled. Clear formulations are possible in respect of the invention formulations because the selected structurant forms a fibrous structure within the liquid hydrophobic carrier that is not seen by the human eye and the RIs of the carrier liquid and the suspended antiperspirant active have been appropriate matched.

It is highly desirable to employ RI matching as indicated above, to enable the resultant composition to transmit at least 1% light (in the test described hereinafter) and especially at least 5%.

Mechanical Properties and Product Packages

The compositions of this invention are structured liquids and are firm in appearance. A composition of this invention will usually be marketed as a product comprising a container with a quantity of the composition therein, where the container has an aperture for the delivery of composition, and means for urging the composition in the container towards the delivery aperture. Conventional containers take the form of a barrel of oval cross section with the delivery aperture at one end of the barrel.

A composition of this invention may be sufficiently rigid that it is not apparently deformable by hand pressure and is suitable for use as a stick product in which a quantity of the composition in the form of a stick is accommodated within a container barrel having an open end at which an end portion of the stick of composition is exposed for use. The opposite end of the barrel is often closed.

Generally the container will include a cap for its open end and a component part which is sometimes referred to as an elevator or piston fitting within the barrel and capable of relative axial movement along it. The stick of composition is accommodated in the barrel between the piston and the open end of the barrel. The piston is used to urge the stick of composition along the barrel. The piston and stick of composition may be moved axially along the barrel by manual pressure on the underside of the piston using a finger or rod inserted within the barrel. Another possibility is that a rod attached to the piston projects through a slot or slots in the barrel and is used to move the piston and stick. Preferably the container also includes a transport mechanism for moving the piston comprising a threaded rod which extends axially into the stick through a correspondingly threaded aperture in the piston, and means mounted on the barrel for rotating the rod. Conveniently the rod is rotated by means of a hand-wheel mounted on the barrel at its closed end, i.e. the opposite end to the delivery opening.

The component parts of such containers are often made from thermoplastic materials, for example polypropylene or polyethylene. Descriptions of suitable containers, some of which include further features, are found in U.S. Pat. Nos. 4,865,231, 5,000,356 and 5,573,341.

Composition Preparation

Compositions of this invention can be produced by conventional processes for making cosmetic solids. Such processes involve forming a heated mixture of the composition at a temperature which is sufficiently elevated that all the structurant dissolves, pouring that mixture into a mould, which may take the form of a dispensing container, and then cooling the mixture whereupon the structurant solidifies into a network of fibres extending through the water-immiscible liquid phase.

A convenient process sequence for a composition which is a suspension comprises first forming a solution of the structurant in the water-immiscible liquid or one of the water-immiscible liquids or a fraction of the liquid or mixture of liquids. This is normally carried out by agitating the liquid, or mixture or fraction at a temperature sufficiently high that all the structurant dissolves (the dissolution temperature) such as a temperature in a range from 50 to 140° C. Thereafter, the particulate antiperspirant active, is blended with the hot mixture or with the remainder of the liquids. This may be done slowly, or the particulate solid is preferably preheated, in order to avoid premature gelation.

The resulting mobile blend comprising suspended particulates, and dissolved structurant can then be introduced into a dispensing container such as a stick barrel. This is usually carried out at a temperature 5 to 30EC above the setting temperature of the composition. The container and contents are then cooled to ambient temperature. Cooling may be brought about by nothing more than allowing the container and contents to cool. Cooling may be assisted by blowing ambient or even refrigerated air over the containers and their contents.

Many of the cosmetic composition according to the present invention employ a mixture of hydrophobic carrier fluids. In some convenient preparative routes, for example those employing an amido structurant, it is desirable to dissolve that structurant in an alcoholic carrier fluid, if such a liquid carrier is employed. As described hereinbefore, such alcoholic carrier comprises a branched aliphatic alcohol, eg isostearyl alcohol or octyldodecanol, optionally in conjunction with an alcohol having some water-miscibility and boiling point above the dissolution temperature of the amido-structurant in the alcoholic fluid, commonly, above 90° C., avoiding high shear mixing that could cause premature gelation. The proportion of the carrier fluids for dissolving the amido structurant is often from 15 to 65% by weight of the carrier fluids, and particularly from 20 to 40%. The antiperspirant active, and any other particulates, if employed, can be blended with the remainder of the carrier fluids, possible with high shear mixing, and such a split process for incorporating structurant and antiperspirant, enables the producer to avoid heating a significant fraction of the composition to a temperature as high as that at which the amido structurant dissolves in the carrier mixture or melts. The two fractions of the carrier can thereafter be mixed, with low shear.

EXAMPLES

Materials

The materials used in the preparation of antiperspirant formulations, their proprietary names and their refractive index (where appropriate) were as shown in Table 1 below:-

TABLE 1

| | | Product | |
|---|---|---|---|
| | Name | Trademark/Supplier | Properties |
| 1 | Isostearyl alcohol (ISA) | Pricerine 3515 ™ ex Uniqema | RI = 1.4559 |
| 2 | 1,1,5,5-tetraphenyl trisiloxane | DC704 ™ ex Dow Corning Inc | RI = 1.5558 |
| 3 | Volatile cyclomethicone | DC 245 ™ ex Dow Corning Inc | RI = 1.3996 |
| 4 | A1 Milled Macrospherical AACH | A418 ™ ex Summit | 20% <10 μm few hollow RI = 1.530 |
| 5 | A2 Milled Macrospherical AACH | Aloxicoll LR ™ : ex Giulini | 15% <10 μm few hollow RI = 1.528 |
| 6 | A3 water modified A2 | as A2 | 12.7% water RI = 1.516 |
| 7 | H1 AACH solution Freeze dried and milled in house | solution of A296 ™ ex BK Giulini | 62% <10:m no hollow RI = 1.528 |
| 8 | H2 AZAG solution, freeze dried and water modified in house | solution of Rezal 67 ™ ex Reheis Inc | 37% <10:m no hollow RI = 1.526 |
| 9 | H3 AZAG solution, freeze dried and water modified in house | as H2 | 37% <10:m |
| 10 | A4 Al/Zr Tetrachlorohydrex glycine, water modified in house | AZAG 7155 ™ ex Summit | 53% <10:m no hollows RI = 1.540 |
| 11 | A5 Al/Zr pentachlorohydrex glycine, | P5G ex BK Giulini | 25% <10:m few hollows RI = 1.530 |
| 12 | N-lauroyl-L-glutamic acid Di-n-butylamide | GP-1 ex Ajinomoto Co Inc | |
| 13 | dibenzylidene sorbitol (BDS) | Roquette | |
| 14 | Lanosterol | ex Croda Ltd | |
| 15 | benzyl alcohol (BMA) | | |

TABLE 1-continued

| | | Product | |
|---|---|---|---|
| | Name | Trademark/Supplier | Properties |
| 16 | $C_{12-15}$ alkyl esters of benzoic acid (TN) | Finsolv TN ™ ex Finetex Inc | |
| 17 | CDS1 | Made in house | |
| 18 | CDS2 | Made in house | |
| 19 | CDS3 | Made in house | |
| 20 | CDS4 | Made in house | |
| 21 | CDS5 | Made in house | |
| 22 | CDS6 | Made in house | |
| 23 | CDS7 | Made in house | |

CDS1 thymol derivative of aspartame based cyclodipeptide
CDS2 3,5-dimethyl cyclohexanol derivative of aspartame based cyclodipeptide
CDS3 1S, 2R, 5S-(+)menthol derivative of aspartame based cyclo dipeptide
CDS4 4-t-butylphenol derivative of aspartame based cyclodipeptide
CDS5 Carveol derivative of aspartame based cyclo dipeptide
CDS6 Carvacrol derivative of aspartame based cyclo dipeptide
CDS7 5,6,7,8 tetrahydronaphth-2-ol derivative of aspartame based cyclo dipeptide
Hollow refers to the nature of the particles.

Preparation of Antiperspirant Actives in House by Freeze Drying and Milling Method Sample Hi—AACH A296 was dissolved at 80° C. in enough water to give a 10% active solution. The solution was then cooled rapidly in an ice bath to about 20° C., poured into a shallow dish, frozen in a freezer, and then freeze dried using a E-C Super Modulyo™ Freeze Drier. The resulting solid material was broken up and then ball milled for 24 hrs. The material was finally passed through a 125:m sieve to remove any coarse lumps.

For Samples H2 and H3, the procedure for H1 was followed except that initially AZAG (Rezal 67) was dissolved in water at room temperature to give a 20% active solution without intervening heating solution.

Water Modification Method

For Samples A3, A4, H2 and H3. A saturated KCl salt solution was placed at the bottom of a dessicator to control the humidity. Powdered antiperspirant active was then placed in a crystallising dish within the dessicator. The powder was stirred intermittently to aid the uniform uptake of the water vapour. The amount of water absorbed by the active powder depended on the salt used (water activity, $a_w$) and the length of exposure time.

Preparation of Materials CDS1 to CDS7

These structurants were made using the following general method in which (2S-cis)-(−)-5-benzyl-3,6-dioxo-2-piperazine acetic acid (DOPAA) was reacted with an alcohol, respectively thymol, 3,5-dimethyl cyclohexanol, 1S, 2R, 5-(+) menthol, 4-t-butylphenol, carveol, carvacrol and 5,6,7,8 tetrahydronaphth-2-ol.

A 250 ml 3 necked round bottomed flask equipped with a stirrer was charged with DOPAA, and dimethyl sulfoxide (8 mls per lg of DOPAA) was then introduced at laboratory ambient temperature (about 22° C.) with stirring. The DOPAA dissolved only partially. 1,1'-carbonyldiimidazole was then introduced with stirring in the amount specified in the Table. Vigorous effervescence occurred and the react mixture was left stirring at room temperature for 45 minutes after which time the reaction mixture went clear. The specified alcohol was stirred into the clear reaction mixture and maintained at 50° C. overnight (between 16 and 20 hours), whereupon it was allowed to cool to ambient temperature (about 22° C.), and poured into water, producing a precipitate which was filtered off and washed with further quantities of water until any residual diimidazole had been removed (as shown by $^1$Hnmr). The washed precipitate was then washed with diethyl ether, except for CB which was washed with toluene. The washed product was dried in a vacuum oven to constant weight.

Stick Characterisation—Measurement of Properties i) Stick hardness—Penetrometer

The hardness and rigidity of a composition which is a firm solid can be determined by penetrometry. If the composition is a softer solid, this will be observed as a substantial lack of any resistance to the penetrometer probe.

A suitable procedure is to utilises a lab plant PNT penetrometer equipped with a Seta wax needle (weight 2.5 grams) which has a cone angle at the point of the needle specified to be 9°10N ∀ 15N. A sample of the composition with a flat upper surface is used. The needle is lowered onto the surface of the composition and then a penetration hardness measurement is conducted by allowing the needle with its holder to drop under a total weight, (i.e. the combined weight of needle and holder) of 50 grams for a period of five seconds after which the depth of penetration is noted. Desirably the test is carried out at a number of points on each sample and the results are averaged. Utilising a test of this nature, an appropriate hardness for use in an open-ended dispensing container is a penetration of less than 30 mm in this test, for example in a range from 2 to 30 mm. Preferably the penetration is in a range from 5 mm to 20 mm.

In a specific protocol for this test measurements on a stick were performed in the stick barrel. The stick was wound up to project from the open end of the barrel, and then cut off to leave a flat, uniform surface. The needle was carefully lowered to the stick surface, and then a penetration hardness measurement was conducted. This process was carried out at six different points on the stick surface. The hardness reading quoted is the average value of the 6 measurements.

ii) Deposition by firm sticks (pay-off)

Another property of a composition is the amount of it which is delivered onto a surface when the composition is drawn across that surface (representing the application of a stick product to human skin), sometimes called the pay-off. To carry out this test of deposition when the composition is a firm stick, able to sustain its own shape, a sample of the composition with standardised shape and size is fitted to apparatus which draws the sample across a test surface under standardised conditions. The amount transferred to the surface is determined as an increase in the weight of the substrate to which it is applied. If desired the colour, opacity or clarity of the deposit may subsequently be determined. A specific procedure for such tests of deposition and whiteness applicable to a firm solid stick used apparatus to apply a deposit from a stick onto a substrate under standardised conditions and then measures the mean level of white deposits using image analysis.

The substrates used were samples of a 12×28 cm strip of black Worsted wool fabric. The substrates were weighed before use. The sticks were previously unused and with domed top surface unaltered.

The apparatus comprised a flat base to which a flat substrate was attached by a clip at each end. A pillar having a mounting to receive a standard size stick barrel was mounted on an arm that was moveable horizontally across the substrate by means of a pneumatic piston.

Each stick was kept at ambient laboratory temperature overnight before the measurement was made. The stick was advanced to project a measured amount from the barrel. The barrel was then placed in the apparatus and a spring was positioned to biassed the stick against the substrate with a standardised force. The apparatus was operated to pass the stick laterally across the substrate eight times. The substrate was carefully removed from the rig and reweighed. The whiteness of the deposit could subsequently be measured as described at (v) below.

(iii) Whiteness of Deposit

The deposits from the at test (ii) above, were assessed for their whiteness shortly after application (ie within 30 minutes) or after an interval of 24 hours approximately.

This was done using a Sony XC77 monochrome video camera with a Cosmicar 16 mm focal length lens positioned vertically above a black table illuminated from a high angle using fluorescent tubes to remove shadowing. The apparatus was initially calibrated using a reference white card, after the fluorescent tubes had been turned on for long enough to give a steady light output. A cloth or Carborundum paper with a deposit thereon from the previous test was placed on the table and the camera was used to capture an image. An area of the image of the deposit was selected and analysed using a Kontron IBAS™ image analyser. This notionally divided the image into a large array of pixels and measured the grey level of each pixel on a scale of 0 (black) to 255 (white). The average of the grey intensity was calculated. This was a measure of the whiteness of the deposit, with higher numbers indicating a whiter deposit. It was assumed that low numbers show a clear deposit allowing the substrate colour to be seen.

iv Clarity of formulation—light transmission

The clarity of a composition may be measured by placing a sample of standardised thickness in the light path of a spectrophotometer and measuring transmittance, as a percentage of light transmitted in the absence of the gel.

This test was carried out using a dual-beam Perkin Elmer Lambda 40 spectrophotometer. The sample of composition was poured hot into a 4.5 ml cuvette made of poly(methylmethacrylate) (PMMA) and allowed to cool to an ambient temperature of 20–25° C. Such a cuvette gives a 1 cm thickness of composition. Measurement was carried out at 580 nm, with an identical but empty cuvette in the reference beam of the spectrophotometer, after the sample in the cuvette had been held for 24 hours. A transmittance measured at any temperature in the range from 20–25° C. is usually adequately accurate, but measurement is made at 22° C. if more precision is required.

Example 1

In this Example, a stick structured with a cyclodipeptide structurant was made by the following general method.

The RI of the antiperspirant active was measured using a Becke line test, (a standard procedure). In a preliminary determination, the proportion of the carrier oils were calculated and the mixture checked by measurement) such that the refractive index of the mixture was closely matched to that of the active. The cyclo-dipeptide was dissolved in isostearyl alcohol (ISA) whilst being heated to about 125° C. to 135° C., and stirred using an overhead paddle stirrer. The DC 704 was heated to 50° C. whilst being stirred using a stirrer bar. The active was added slowly to the DC704. When all the active had been added, the mixture was sheared using a Silverson mixer at 7000 rpm for 5 minutes. The dispersion of antiperspirant active in the non-volatile silicone oil was heated in an oven at 85° C. The structurant solution in ISA was allowed to cool to 90° C., and the active mixture was added. The temperature of the beaker was kept constant at 85° C., the mixture was stirred thoroughly and poured into stick barrels immediately and allowed to cool.

The composition and properties of the stick are summarised in Table 2.

TABLE 2

| Ingredient | Ex 1 % by weight |
|---|---|
| ISA (1) | 18.34 |
| DC704 (3) | 55.03 |
| A1 (4) | 25.12 |
| CDS1 (12) | 1.51 |
| Properties | |
| Hardness (mm) | 23 |
| Clarity (% T) | 44 |

Example 2

In this Example, the sticks were structured with a combination of a cyclodipeptide and an N-acyl aminoacid amide. The sticks were made by the same general method as for Example 1, except that the structurants were dissolved separately in the ISA component of the carrier liquid mixture, the CDS structurant before GP-1, and the fluid mixture was poured into stick barrels at about 75° C. rather than about 85° C.–90° C.

The composition and properties of the sticks are summarised in Table 3 below.

TABLE 3

| Ingredient | % by weight | | | | |
|---|---|---|---|---|---|
| Example No | 2.1 | 2.2 | 2.3 | 2.4 | 2.5 |
| ISA (1) | 17.61 | 17.36 | 17.55 | 17.61 | 16.71 |
| DC704 (2) | 52.89 | 52.14 | 52.7 | 52.89 | 54.29 |
| A1 (4) | 25.0 | 25.0 | 25.0 | 25.0 | |
| H2 (8) | | | | | 25.0 |
| CDS1 (17) | 1.5 | 1.5 | | | 1.0 |
| CDS2 (18) | | | 0.70 | | |
| CDS3 (19) | | | | 1.0 | |
| GP-1 (12) | 3.0 | 4.0 | 4.05 | 3.5 | 3.0 |
| Properties | | | | | |
| Hardness (mm) | 14.7 | 13.1 | 16.1 | 14.8 | 16.2 |
| Clarity (% T) | 12.7 | 15.3 | 12.0 | 9.9 | 0.7 |
| Pay-off (initial) | 0.88 | 0.54 | 0.92 | 0.58 | 0.83 |
| Visible Deposits 24 hr) | 15 | 17 | 20 | 17 | 17 |
| Example No | 2.6 | 2.7 | 2.8 | 2.9 | 2.10 |
| CDS1 (17) | 2.81 | | 1.5 | 1.7 | 1.5 |
| CDS4 (20) | | 3.0 | | | |
| GP-1 (12) | | | 2.0 | | 4.0 |
| DBS (13) | | | 0.25 | 0.4 | |
| ISA (1) | 8.81 | | 17.8 | 18.46 | 15.735 |
| DC704 (2) | 42.36 | 29.47 | 53.45 | 52.48 | 53.765 |
| BMA (15) | 8.81 | 19.68 | | 1.96 | |
| TN (16) | 12.21 | 22.83 | | | |
| A1 (4) | 25.0 | 25.0 | 25.0 | 25.0 | |
| A5 (11) | | | | | 25.0 |
| Properties | | | | | |
| Hardness (mm) | 14.0 | 20.1 | 13.5 | 17.2 | 12.1 |
| Clarity (% T) | 23.0 | 6.1 | 19.4 | 15.3 | 2.2 |
| Clarity (visual score) | n/d | n/d | 2 | 3 | −9 |

TABLE 3-continued

| Ingredient | % by weight | | | | |
|---|---|---|---|---|---|
| Example No | 2.11 | 2.12 | 2.13 | 2.14 | 2.15 |
| CDS1 (17) | 1.7 | 2.0 | | | |
| CDS5 (21) | | | 1.0 | | |
| CDS6 (22) | | | | 0.7 | |
| CDS7 (23) | | | | | 0.4 |
| GP-1 (12) | 2.0 | 2.0 | 4.0 | 4.0 | 4.0 |
| ISA (1) | 16.14 | 17.98 | 15.848 | 15.916 | 15.32 |
| DC704 (2) | 55.16 | 51.1 | 54.152 | 54.384 | 53.30 |
| BMA (15) | | 1.92 | | | 1.98 |
| A1 (4) | | 25.0 | 25.0 | 25.0 | 25.0 |
| A5 (11) | 25.0 | | | | |
| Properties | | | | | |
| Hardness (mm) | 14.4 | 14.2 | 13.7 | 14.2 | 16.9 |
| Clarity (% T) | 13.2 | 26.6 | 27.5 | 15.0 | 8.7 |
| Clarity (visual score) | 7 | 6 | 4 | 1 | 0 |

The sticks containing GP-1 as a co-structurant are harder, but less clear than those formed using the Cyclo Peptides alone. The clarity is however good enough.

Example 3

In this Example sticks are made using the same general method as Example 2, but using an N-acyl aminoacid amide as sole structurant. The composition and properties of the sticks are summarised in Table 4 below.

TABLE 4

| Ingredients Example/ Comparison | % by weight | | | | | |
|---|---|---|---|---|---|---|
| | 3.1 | 3.2 | 3.3 | 3.4 | C3.1 | C3.2 |
| GP-1 (11) | 5.0 | 5.0 | 5.0 | 5.0 | 5.0 | 5.0 |
| ISA (1) | 17.49 | 17.49 | 17.49 | 15.848 | 17.49 | 11.15 |
| DC704 (3) | 52.51 | 52.51 | 52.51 | 54.152 | 52.51 | 58.85 |
| A1 (4) | 25.0 | | | | | |
| A2 (5) | | 25.0 | | | | |
| H1 (7) | | | | | 25.0 | |
| H3 (9) | | | 25.0 | | | |
| A4 (10) | | | | | | 25.0 |
| A5 (11) | | | | 25.0 | | |
| Properties | | | | | | |
| Hardness (mm) | 15.9 | 16.2 | 15.1 | 15.82 | 15.2 | 14.8 |
| Clarity (% T) | 5.9 | 5.2 | 1.8 | 1.9 | 0.37 | 0.07 |
| Pay-off (initial) | 0.97 | 0.51 | 0.80 | n/d | 0.67 | 0.60 |
| Visible Deposits (24 hr) | 13 | 18 | 17 | n/d | 21 | 20 |

From Table 4, it can be seen after consulting the list of ingredients that both the particle size distribution and the chemical nature of the active are important in determining whether or not the resultant antiperspirant suspension product is clear.

A comparison of Ex3.1 with Comparison C3.1 having formulations that differ in the particle size distribution of the antiperspirant active shows a drop in light transmission from 5.9% which is sufficiently clear to read moderately small letters through the sample to a virtually opaque product in Comparison C3.1. Similarly, a comparison of Example 3.3 with Comparison C3.2 shows a drop in light clarity from 1.8% transmission to virtually nothing. The significant difference between the two formulations resides in the particle size distribution of the antiperspirant active, because the active and carriers were similarly and very closely matched to within 0.005 in each sample.

Example 4

In this Example, a clear product was obtained using a sterol structurant. It was made by the following process:-

The RI of the antiperspirant active was measured using a Becke line test, (a standard procedure). In a preliminary determination, the proportions of the carrier oils were calculated such that the refractive index of the mixture was closely matched to that of the active and the RI of the resultant mixture was checked by measurement.

The lanosterol was dissolved in about 60% of the DC704 whilst being heated and stirred using an overhead paddle stirrer. The remaining DC 704 and the DC245 were combined and the mixture was heated to 50° C. whilst being stirred using a. stirrer bar. The active was added slowly to the DC704/DC245 mixture. When the entire active had been added the mixture was sheared using a Silverson mixer at 7000 rpm for 5 minutes. The active dispersion was heated in an oven at 85° C. The lanosterol solution was allowed to cool to 90° C., and the active suspension in DC704/DC245 mixture was added. The resultant mixture was stirred thoroughly and when it had cooled to 700C was poured into stick barrels and allowed to cool to ambient. The ingredients and properties of the composition are summarised in Table 5 below.

TABLE 5

| Example<br>Ingredient | 4.1<br>% by weight |
|---|---|
| DC704 (2) | 51.0 |
| DC245 (4) | 18.0 |
| A3 (6) | 26.0 |
| Lanosterol (16) | 5.0 |
| Properties | |
| Hardness (mm) | 11.3 |
| Clarity (% T) | 10.9 |

What is claimed is:

1. A clear anhydrous solid antiperspirant composition comprising from 1 to 30% by weight of a particulate antiperspirant salt suspended in a water-immiscible liquid carrier that is solidified by an effective amount of a structurant wherein:-
   i) the particulate antiperspirant contains less than 50% by weight of particles having a diameter of up to 10 m and a refractive index of from 1.49 to 1.57 at 22° C.,
   ii) at least 50% by weight of the carrier liquid is selected from liquid non-volatile silicone oils and liquid alkyl-aryl esters
   iii) not more than 25% by weight of the carrier liquid comprises a volatile silicone oil,
   iv) the carrier liquid and the antiperspirant have refractive indexes which differ by no more than 0.02 at 22° C. and
   v) the structurant comprises a fibre-forming non-polymeric structurant.

2. A composition according to claim 1 in which the refractive indexes of the antiperspirant and the carrier liquid differ by no more than 0.01 at 22° C.

3. A composition according to claim 2 in which the antiperspirant and the carrier liquid differ by not more than 0.005 at 22° C.

4. A composition according to claim 1 in which the fibre-forming non-polymeric structurant is an amide or lanesterol.

5. A composition according to claim 4 in which the amide structurant is selected from cyclodipeptides and N-acyl aminoacid amides.

6. A composition according to claim 5 in which the amide structurant comprises a cyclic dipeptide satisfying the following general formula

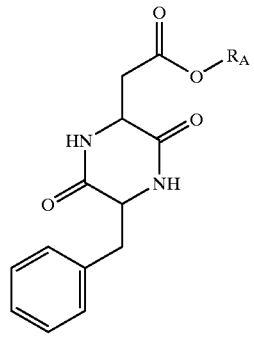

in which $R_A$ represents a carbocyclic or heterocyclic group containing not more than 2 rings.

7. A composition according to claim 6 in which $R_A$ represents a 6 membered carbocyclic ring that is optionally substituted by 1 to 3 alkyl groups, each independently containing 1 to 3 carbon atoms.

8. A composition according to claim 7 in which the residue $R_A$ is derivable from thymol or a 3,5-dialkylcyclohexanol.

9. A composition according to claim 6 in which the amide structurant comprises N-Lauroyl-L-glutamic acid di-n-butylamide.

10. A composition according to claim 6 in which the amide structurant comprises a mixture of the cyclic dipeptide and the N-acyl aminoacid amide in a weight ratio of from 1:12 to 1:1.

11. A composition according to claim 6 in which the amide structurant or mixture of amide structurants is present in an amount of from 1 to 7.5% by weight of the composition.

12. A composition according to claim 11 in which the amide structurant or mixture of amide structurants is present in an amount of from 2 to 6% by weight of the composition.

13. A composition according to claim 6 in which the amide structurant or mixture of amide structurants is present in an amount of from 2 to 12% by weight of the water-immiscible liquid carrier.

14. A composition according to claim 13 in which the amide structurant or mixture of amide structurants is present in an amount of from 4 to 8% by weight of the water-immiscible liquid carrier.

15. A composition according to claim 1 in which the liquid carrier comprises at least 65% by weight of liquid non-volatile silicone oils and liquid alkyl-aryl esters.

16. A composition according to claim 15 in which the liquid carrier comprises up to 85% by weight of liquid non-volatile silicone oils and liquid alkyl-aryl esters.

17. A composition according to claim 1 in which at least 60% by weight of the non-volatile silicone oil comprises an aryl-substituted silicone oil having a refractive index of at least 1.5.

18. A composition according to claim 1 in which the liquid carrier comprises a liquid branched chain aliphatic alcohol.

19. A composition according to claim 18 in which the liquid branched chain aliphatic alcohol comprises isostearyl alcohol.

20. A composition according to claim 18 in which the branched chain aliphatic alcohol comprises from 10 to 35% by weight of the liquid carrier.

21. A composition according to claim 16 in which the carrier mixture contains from 70 to 85% by weight of an aryl-substituted silicone oil having a refractive index of at least 1.5.

22. A composition according to claim 1 in which the at the liquid carrier is free from alkoxy cinnamates.

23. A composition according to claim 1 in which the antiperspirant comprises not more than 25% by weight of particles having a particle diameter of up to 10 $\mu$m.

24. A composition according to claim 1 in which the antiperspirant is an activated aluminium chlorohydrate.

25. A composition according to claim 1 in which the antiperspirant is zirconium-containing.

26. A composition according to claim 1 which has a light transmission at a wavelength of 580 nm at 22° C. of at least 1%.

27. A composition according to claim 26 which has a light transmission at a wavelength of 580 nm at 22° C. of at least 5%.

28. An antiperspirant product comprising a dispensing container having an aperture for delivery of the contents of the container, means for urging the contents of the container through the said aperture, and an antiperspirant composition stored within the container between the aperture and the urging means, characterised in that the antiperspirant composition is in accordance with the composition described in claim 1.

29. A method of making an antiperspirant composition comprising the steps of:

a1) incorporating into a water-immiscible liquid carrier a structurant which is one or more structurant compounds as defined in the composition of the first aspect, a2) mixing the liquid carrier with a particulate antiperspirant active as described in the first aspect, a3) heating the liquid carrier or a mixture containing it to an elevated temperature at which the structurant is dissolved or dispersed in the water-immiscible liquid carrier, steps a1) a2) and a3) being conducted in any order followed by:

b1) introducing the mixture into a mould which preferably is a dispensing container, and then c1) cooling or permitting the mixture to cool to a temperature at which the liquid carrier is solidified, in which the resultant composition is in accordance with the composition described in claim 1.

30. A method according to claim 29 in which the liquid carrier comprises a mixture of liquids including a liquid water-immiscible aliphatic alcohol and the structurant comprises at least one amido structurant and in step a1, the structurant is introduced into a fraction of the carrier mixture containing the liquid water-immiscible aliphatic alcohol at elevated temperature and low shear mixing.

31. A method according to claim 30 in which in step a2, the antiperspirant active is introduced into a second fraction of the carrier mixture which is combined with the fraction of carrier mixture containing the structurant before step b1.

32. A cosmetic method for preventing or reducing perspiration or odour formation on human skin comprising topically applying to the skin a composition comprising an antiperspirant active, a water-immiscible liquid carrier and a structurant compound as described in accordance with claim 1.

* * * * *